(12) United States Patent
Isenberg

(10) Patent No.: US 10,238,448 B2
(45) Date of Patent: Mar. 26, 2019

(54) SURGICAL DEVICES AND MECHANISMS

(71) Applicant: Medtronic, Inc., Minneapolis, MN (US)

(72) Inventor: John Isenberg, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 310 days.

(21) Appl. No.: 14/853,903

(22) Filed: Sep. 14, 2015

(65) Prior Publication Data

US 2016/0000497 A1     Jan. 7, 2016

Related U.S. Application Data

(62) Division of application No. 13/247,198, filed on Sep. 28, 2011, now Pat. No. 9,161,805.

(51) Int. Cl.
*A61B 18/14*     (2006.01)
*A61B 17/00*     (2006.01)
(Continued)

(52) U.S. Cl.
CPC .... *A61B 18/1445* (2013.01); *A61B 17/00234* (2013.01); *A61B 18/1447* (2013.01); *A61B 2017/00318* (2013.01); *A61B 2017/2903* (2013.01); *A61B 2017/2905* (2013.01); *A61B 2017/2916* (2013.01);
(Continued)

(58) Field of Classification Search
CPC .............. A61B 18/085; A61B 18/1442; A61B 18/1445; A61B 18/1447; A61B 18/1492; A61B 2018/00577; A61B 2018/00595; A61B 17/28; A61B 17/29; A61B 17/2909; A61B 2017/00336; A61B 2017/00738; A61B 2017/2902; A61B 2017/2903; A61B 2017/2905; A61B 2017/2919; A61B 2017/2926; A61B 2017/2929; A61B 2017/2932; A61B 2017/2933; A61B 2017/2936; A61B 2017/2944

See application file for complete search history.

(56) References Cited

U.S. PATENT DOCUMENTS 5,496,333 A   3/1996   Sackier et al.
5,792,178 A   8/1998   Welch et al.
(Continued)

FOREIGN PATENT DOCUMENTS

WO    WO 2008/045348 A2    4/2008

OTHER PUBLICATIONS

EPC Communication dated Aug. 11, 2017 in corresponding EP Appln.No. 127653627.4.

*Primary Examiner* — Todd Scherbel
(74) *Attorney, Agent, or Firm* — Dicke, Billig & Czaja, PLLC

(57) ABSTRACT

An instrument for use in a medical procedure that includes a proximal end, a distal end, a handle adjacent to the proximal end of the instrument, a flexible elongated neck extending distally from a distal end of the handle, a jaw power screw extending from a distal end of the neck, a pair of moveable jaws operatively connected to the jaw power screw, and a handle power screw assembly operatively connected to a proximal end of the flexible neck within the handle, wherein manipulation of the handle will control movement of the jaws.

12 Claims, 5 Drawing Sheets

(51) Int. Cl.
  *A61B 17/29* (2006.01)
  *A61B 18/00* (2006.01)
(52) U.S. Cl.
  CPC ............... *A61B 2017/2919* (2013.01); *A61B 2017/2936* (2013.01); *A61B 2017/2944* (2013.01); *A61B 2018/00404* (2013.01); *A61B 2018/00577* (2013.01); *A61B 2018/00595* (2013.01); *A61B 2018/145* (2013.01)

(56) References Cited

U.S. PATENT DOCUMENTS

| | | |
|---|---|---|
| 7,367,976 B2 * | 5/2008 | Lawes ............... A61B 18/1445 606/41 |
| 7,967,816 B2 | 6/2011 | Ocel et al. |
| 8,403,945 B2 | 3/2013 | Whitfield et al. |
| 8,568,425 B2 | 10/2013 | Ross et al. |
| 2010/0087818 A1 | 4/2010 | Cunningham |
| 2010/0185232 A1 | 7/2010 | Hughett, Sr. et al. |

* cited by examiner

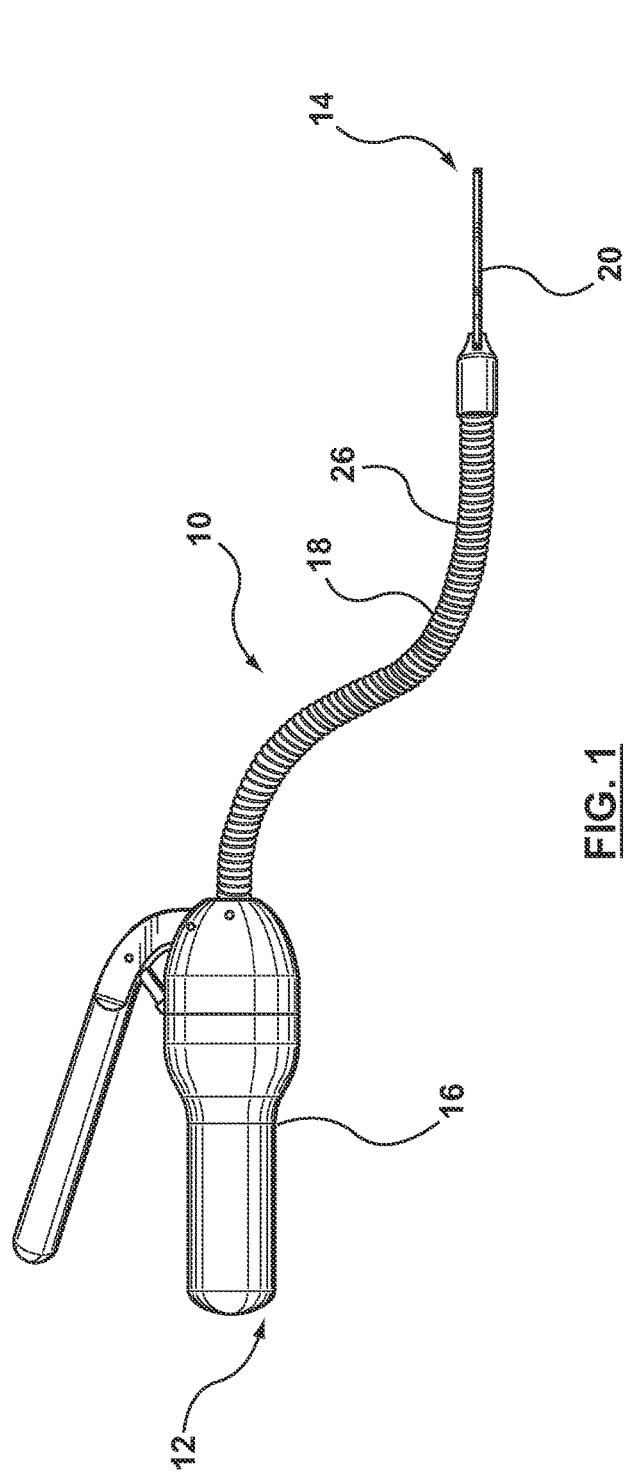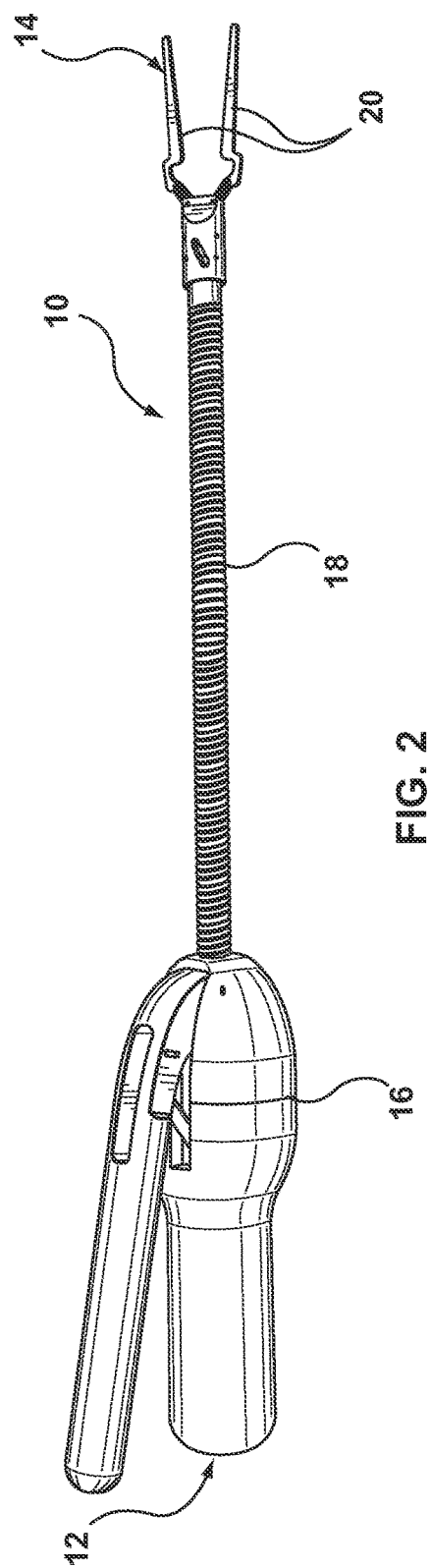

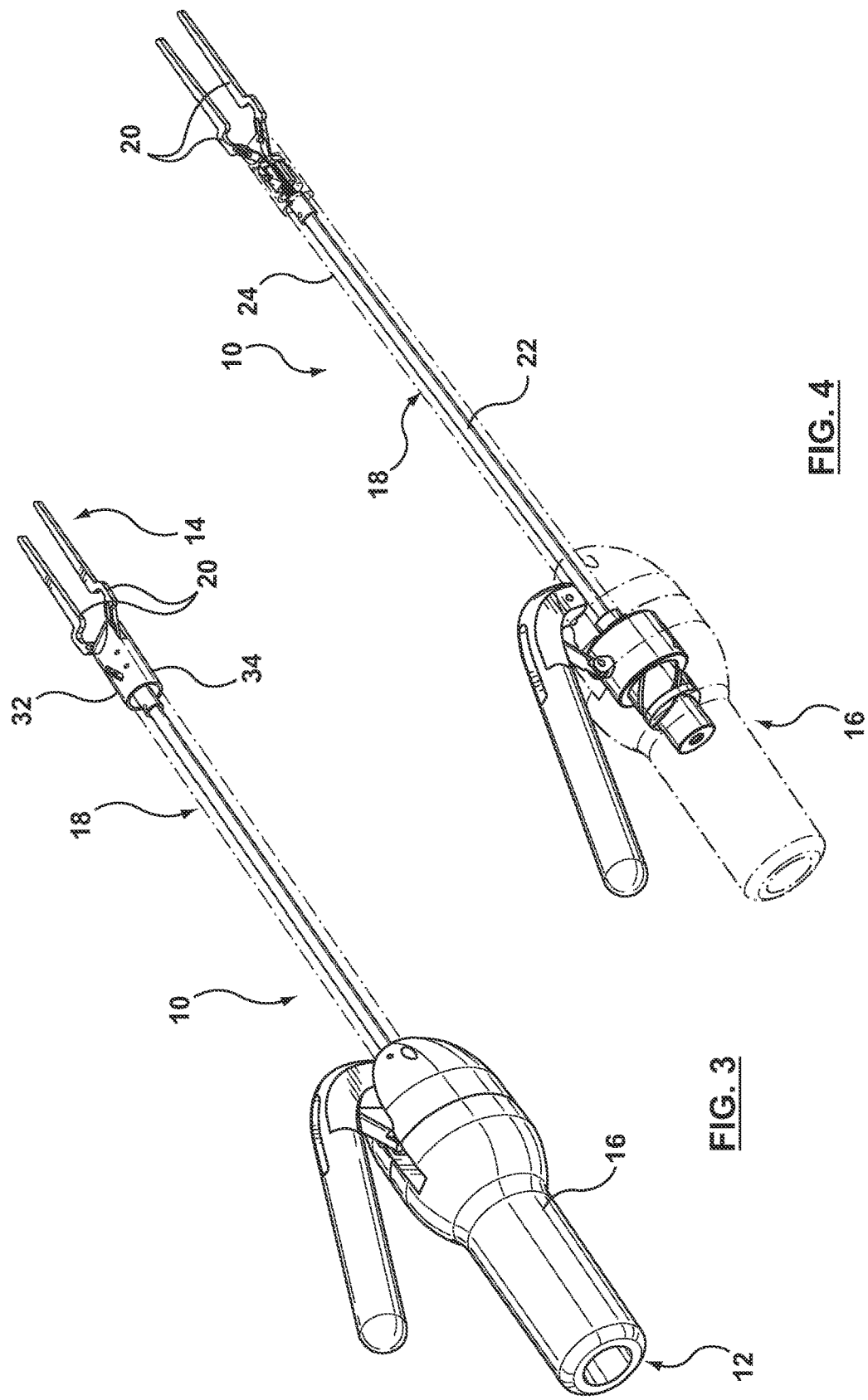

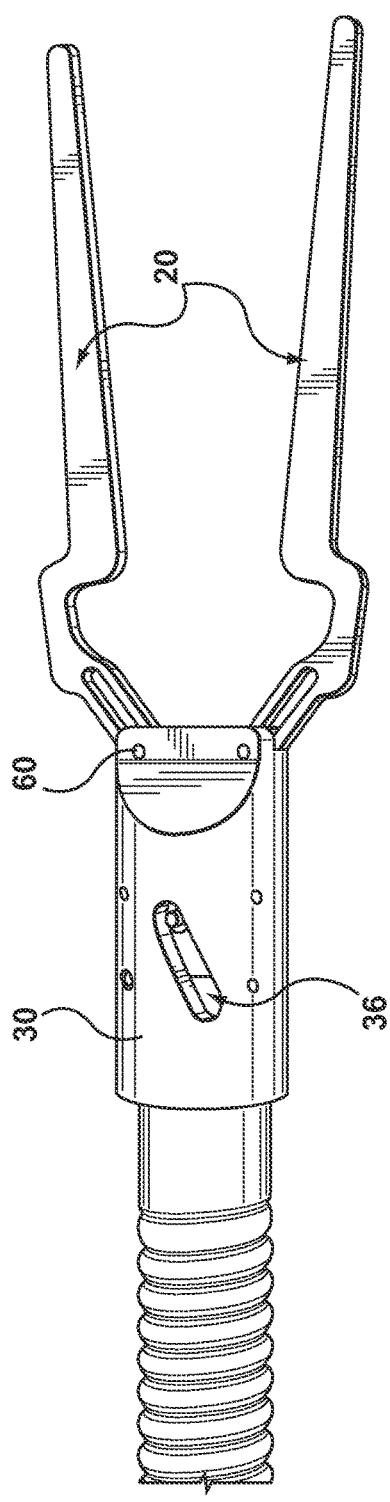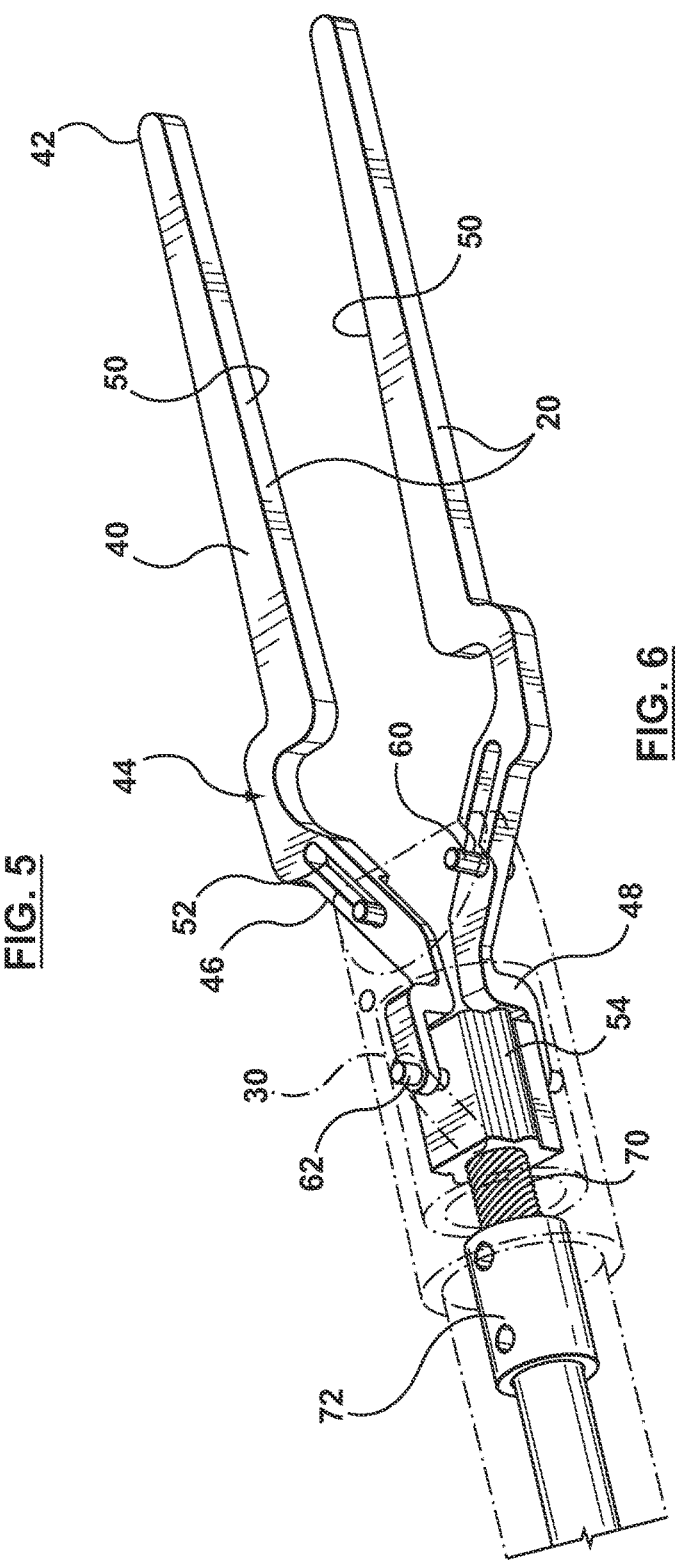

SURGICAL DEVICES AND MECHANISMS

RELATED APPLICATIONS

This application is a Division of and claims the benefit of U.S. patent application Ser. No. 13/247,198 filed Sep. 28, 2011, now allowed. The disclosures of which are herein incorporated by reference in their entirety.

TECHNICAL FIELD

The present invention relates to surgical devices and mechanisms for accessing a surgical site in a patient, and more particularly relates to electrosurgical devices and mechanisms used for surgical ablation and/or cauterization procedures in a surgical site in a patient.

BACKGROUND

Tissue ablation and/or cauterization are common techniques used for the surgical treatment of cardiac arrhythmia, such as atrial fibrillation. In general terms, cardiac arrhythmia relates to disturbances in the heart's electrical system that cause an abnormal heartbeat. Irregular heartbeats, or arrhythmia, can be caused by physiological or pathological disturbances in the discharge of electrical impulses from the sinoatrial node or in the transmission of the signal through heart tissue, or by spontaneous, unexpected electrical signals generated within the heart. One specific type of arrhythmia is atrial fibrillation, in which instead of a single beat, numerous electrical impulses are generated by depolarizing tissue at one or more locations in the atria or other locations in the heart. These unexpected electrical impulses produce irregular, often rapid heartbeats in the atria. In order to overcome this problem, ablation of the abnormal tissue or accessory pathway responsible for the atrial fibrillation can be an effective treatment. The locations of such tissue ablation can vary, depending on the particular pathway irregularities and the desired surgical outcomes to be achieved.

Regardless of the exact application, ablation or cauterization of tissue can be achieved by applying ablative energy to target tissue, which may include radiofrequency electrical energy, direct current electrical energy, and the like. In such cases, the ablative energy can be delivered by an electrode that is placed in contact with the target tissue, for example. For some treatments, the electrode can be formed as a part of a catheter that is subcutaneously delivered to the target site. However, such catheters are often designed to be able to travel long distances and through complicated pathways in a patient, and therefore can be too flexible to be able to achieve precise placement of the electrodes relative to the target tissue.

Hand-held electrosurgical systems can alternatively be used, in order to overcome disadvantages of catheter-based devices. Such electrosurgical instruments can include a hand-held instrument capable of ablating tissue or cauterizing tissue, but does not include an elongated, flexible delivery catheter. The hand-held instrument can be comparatively short to provide a more rigid attachment of the electrode tip to the instrument's handle for precise manipulation by a surgeon. The rigid construction of the electrosurgical instrument requires relatively direct, open access to the targeted tissue. Thus, for treatment of atrial fibrillation via an electrosurgical instrument, it can be desirable to gain access to the patient's heart through one or more openings in the patient's chest (such as via a sternotomy, a thoracotomy, a small incision, a port, and/or the like). In addition, the patient's heart may be opened through one or more incisions, thereby allowing access to the endocardial surface of the heart.

Once the target site (e.g., right atrium, left atrium, epicardial surface, endocardial surface, etc.) is accessible, the surgeon can position the electrode tip of the electrosurgical instrument at the target site. The tip is then energized, allowing the tip to ablate or cauterize the contacted tissue. A desired lesion pattern can then be created by moving the tip to particular locations relative to the target site. Due to the relatively short and rigid construction of many hand-held instruments described above, a surgeon can control the exact positioning and movement of the tip to achieve a desired ablation result.

With many of these hand-held electrosurgical instruments, however, a particular directional orientation is designed or chosen to achieve a certain ablation pattern. For example, the instrument can include a handle from which a rigid neck member (with a distal tip) extends with a preset curvature. This permanent curvature is provided in some cases to facilitate the particular procedure for which the electrosurgical instrument is intended, such as ablation of a desired lesion pattern. While such an approach may work well for certain patients, the same instrument may not be optimal for use to reach the same anatomical locations of other patients. In addition, instruments with such a preset configuration may only be useful in a very specific area of a patient, such that it is not useful or applicable for other areas of the patient.

As discussed above, electrosurgical instruments can be highly useful for performing a variety of surgical procedures, including surgical treatment of atrial fibrillation. However, instruments that include a permanent curve or other shape variation into the instrument itself may limit the usefulness of the device to a limited number of very specialized procedures. Therefore, there is a need to provide ablation and/or cauterization instruments that can be reconfigured and which also includes controlling features at a proximal end of the instrument to allow for control of jaws or other features that are positioned at the distal end of the device. There is also a need to control jaws of a device when accessing epicardial surfaces via a subxiphoid access approach.

SUMMARY

In one aspect of this invention, an instrument is provided, which is described generally herein as an ablation device or tool, which includes a surgical device that is used to create lesions on a surface of the heart, such as to create lesions on the epicardial surface of the heart. This can be accomplished using irrigated radiofrequency energy, for example. In one particular use of this ablation device or tool, a subxiphoid approach is used to access the desired area of the heart, therefore, the ablation device is provided with a somewhat flexible or reconfigurable neck to facilitate placement of its jaws around the pulmonary veins of the patient. This is accomplished by guiding the jaws along the epicardial surface of the heart during the process of placing or positioning it in a desired location. However, the jaws can also be in an at least partially closed configuration as they are moved along the surfaces of the heart and lungs.

In an aspect of the invention, an ablation device includes an elongated flexible neck. In order to overcome the friction introduced into the system when this neck is flexed or reconfigured, one or more jaw mechanisms are configured to allow for active jaw opening and closing. In this configuration, the jaws can be pushed and pulled for jaw control, rather than just being pulled, which can be accomplished by using a flexible shaft within a flexible neck that is driven by a 4-bar linkage in the device handle, with power screws on either end (i.e., a power screw assembly).

The power screw assemblies of the devices of the invention can include a mechanism that consists essentially of power screws and a flexible shaft. The power screw assembly includes ball bearings and applies torque to clamp the jaws at the distal end of the device. The power screw assembly also includes return springs that can be used for opening the jaws, but such springs are not required for opening the jaws. Rather, the handle assembly of the device can be used to rotate or push the power screw assembly until the jaws are completely open. This power screw assembly opens and closes the jaw both by translational movement and by rotational movement. In this embodiment, rotation typically occurs after the translational limits are reached. That is, linear motion in the handle of the device is converted into rotational motion, which is converted back into linear motion in the jaw mechanism. Thus, the devices of the invention include the capability to actively open the jaws on the device to facilitate accurate placement relative to target tissue.

Although a subxiphoid access approach to reach target tissue is discussed herein, it is understood that the device can instead or additionally be used in other areas of the heart and/or other areas of the body in which ablation or cauterization procedures are to be performed. To that end, a number of different configurations of surgical devices are within the scope of the invention, where such configurations can include devices having multiple jaws, differently configured jaws, and/or longer or shorter neck portions that can be more or less flexible than described herein. Other variations are also possible while still utilizing the functional aspects described herein.

BRIEF DESCRIPTION OF THE DRAWINGS

The present invention will be further explained with reference to the appended Figures, wherein like structure is referred to by like numerals throughout the several views, and wherein:

FIG. 1 is a front view of an ablation device in accordance with an embodiment of the invention;

FIG. 2 is a top perspective view of the ablation device of FIG. 1;

FIG. 3 is a perspective view of an ablation device of the invention;

FIG. 4 is a perspective view of the ablation device of FIG. 3, in which certain components are shown as being opaque or transparent in order to provide a better view of the interior components;

FIG. 5 is a top view of a distal end of an ablation device of the invention, which includes moveable jaws in an open position;

FIG. 6 is a perspective view of a distal end of an ablation device of the invention, in which certain components are shown as being opaque or transparent in order to provide a better view of the interior components;

DETAILED DESCRIPTION

Figure 7:
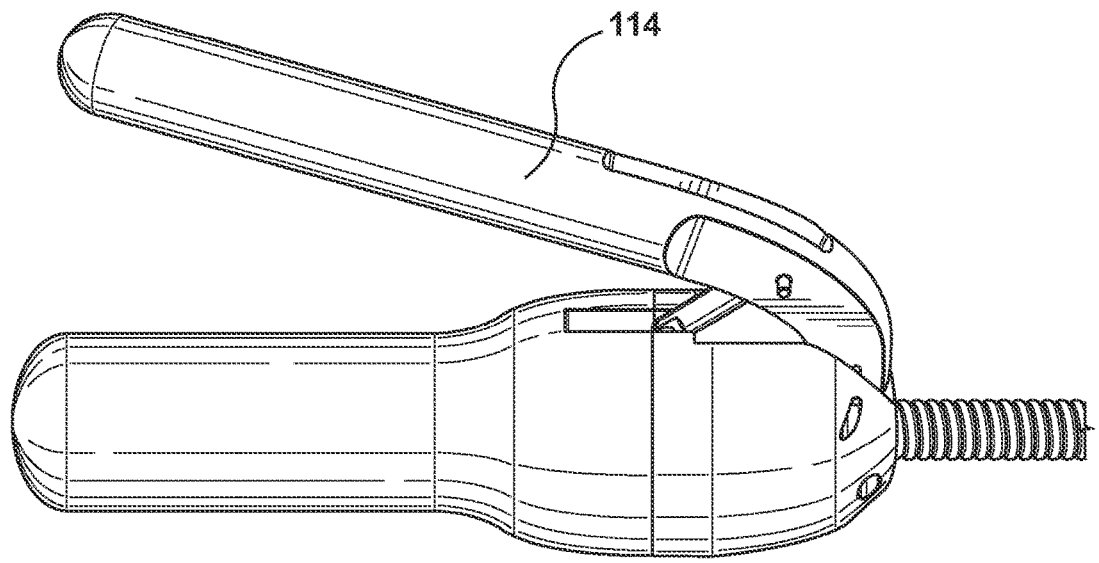
FIG. 7 is a front perspective view of a proximal or handle portion of an ablation device of the invention.

Referring now to the Figures, wherein the components are labeled with like numerals throughout the several Figures, and initially to FIGS. 1 and 2, one embodiment of an instrument or ablation device 10 of the invention is illustrated, which generally includes a proximal end 12, a distal end 14, a handle 16 at the proximal end 12, a flexible elongated neck 18 extending distally from the handle 16, and a pair of jaws 20 extending distally from the neck 18. Referring additionally to FIGS. 3 and 4, the elongated neck 18 further includes a flexible elongated shaft 22 extending along its length that is generally surrounded by a flexible tubular cover 24. The tubular cover 24 may be a tube made of plastic or another flexible biocompatible material, which is designed to fit inside an outer tube 26 of the elongated neck 18. The outer tube 26 may be a tube made of metal or another biocompatible material, and may be corrugated, as shown, or may alternatively have a relatively smooth or differently textured outer surface. In any case, the combination of the flexible shaft 22, the tubular cover 24, and the outer tube 26 can be designed and/or selected to provide a desired overall flexibility for the neck 18. That is, it may be desirable in some cases to require a relatively small amount of force to reconfigure the neck 18, while in other cases it may be more difficult to reconfigure the neck 18 (e.g., a tool or other instrument may be necessary to reconfigure the neck).

In embodiments of the invention, the neck can be reconfigured multiple times into different configurations, such as for use in different areas of a patient and/or if it is determined that an initial configuration of the neck is not optimal. It is further understood that the neck can be shaped to have multiple bends or contours along its length and/or to have bends or contours that are in more than one plane (e.g., along the x, y, and/or z axes of the device relative to a longitudinal axis of the device). It is even further understood that the neck need not be bent or contoured at all, but that it is instead straight such that it extends generally along the longitudinal axis of the device. Once the neck in its desired configuration, it is desirable that it can independently maintain this shape until a deliberate external force is applied to reconfigure it.

FIGS. 5 and 6 provide enlarged views of the distal end 14 of the ablation device 10, which includes a pair of jaws 20 that extend from a casing 30 that will be described in further detail below. The jaws 20 of this embodiment each include an elongated portion 40 that extends proximally from a distal tip 42, a contoured or clearance portion 44, an angled portion 46, and a connection flange 48. Each of these portions of the jaws 20 can be selected or designed to provide access, and/or to prevent interference with portions of the anatomy that will be encountered along the travel path to the target tissue.

With regard to this general configuration, however, each of the elongated portions 40 can be designed to have a constant width along its length, or one or both of the elongated portions 40 can have at least a slight taper, as illustrated, to distribute clamping force along their lengths.

The contoured or clearance portion 44 of each of the jaws 20 can be designed to allow access to a particular area of the anatomy, to be able to clamp a particular anatomical feature between the jaws, to provide a clearance area that will not interfere with certain tissues or structures, and/or to provide other surgical advantages. The angled portion 46 of each of the jaws 20, which extends proximally from the clearance portion 44 (and at an angle relative to the longitudinal axis of the device), can be designed in cooperation with the other portions of the jaws to accomplish similar purposes as the clearance portions 44. In addition, each of the angled portions 46 further includes a slot 52 that extends along at least a portion of its length, with which a pin 60 of the casing 30 engages to allow for controlled movement of the jaws 20, as will be described below. Each of the pins 60 can have a diameter that is only slightly smaller than a width of its corresponding slot 52 so that the pin 60 will contact both edges of the slot 52 during relative movement, thereby helping to provide precise control of the jaws during the desired surgical treatment procedures.

The connection flanges 48 of each of the jaws 20 can each extend from the proximal end of the angled portions 46 for connection of its respective jaw 20 to a jaw slider block 54. In the embodiment illustrated in FIGS. 5 and 6, each of the jaws 20 is attached to an opposite side (e.g., top or bottom) of the jaw slider block 54, while top and bottom surfaces of the jaws themselves are arranged to be generally in the same plane as each other. In order to provide such a configuration, each of the connection flanges 48 includes bends or contours that allow it to extend from its respective angled portion 46 and to connect to one of the sides of the jaw slider block 54. The connection flange 48 can have a wide variety of different configurations that provide a desired connection between the jaw 20 and the jaw slider block 54, where different configurations would be particularly applicable if the jaw slider block 54 is differently sized or shaped than is shown. In any case, the connection flanges 48 each include an aperture that can accept a pin 62 for attachment of each jaw 20 to a surface of the slider block 54.

The above described and illustrated embodiment of these jaws 20 is only one exemplary embodiment of a jaw design that can be useful in an ablation device of the invention, wherein a number of variations of these jaws are considered to be within the scope of the invention. For example, the different portions of the jaw between its proximal and distal ends can be relatively longer or shorter than shown, the angles of various jaw portions relative to each other can be different, the jaws may not have a contoured portion (e.g., if the device will be used in an area of the body where such a configuration is not desirable), the jaws may include more or differently shaped and sized contoured portions, or can include any of a wide number of other variations.

The casing 30 provides support for the proximal end of the jaws 20 and also allows the jaws 20 to translate in an axial direction relative to the ends of the device, while their inner surfaces 50 move toward and away from each other. In particular, the casing 30 includes a first portion 32 and a second portion 34, which are shown in the figures as top and bottom pieces 32, 34 (see FIG. 3) of the casing 30, respectively. Each of these portions 32, 34 includes an elongated channel or slot 36 in which one of the pins 62 (which is also used for attachment of one of the jaws 20 to the jaw slider block 54) can slide. Each of the pins 62 can have a diameter that is only slightly smaller than a width of its corresponding channel 36 such that the pin 62 will contact both edges of the channel 36 during relative movement, or can instead have a considerably smaller diameter (as can be seen in FIG. 5) so that the pin 62 can also move laterally within the slot 36 during movement of the jaw 20.

Figure 10:
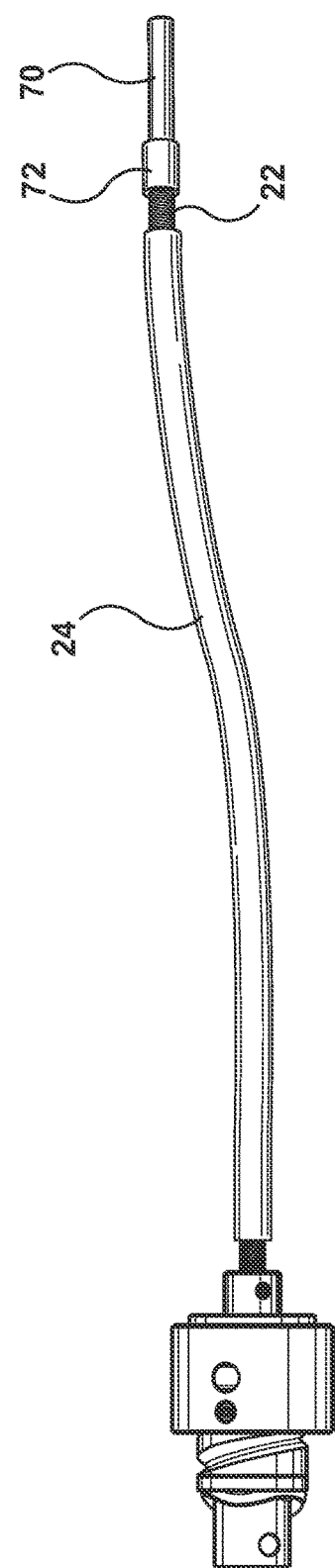
FIG. 10 is a perspective view of certain components of an ablation device of an embodiment of the invention, including a proximal handle power screw, a flexible shaft that is located within a flexible tubular cover and elongated neck, and a distal jaw power screw.

The proximal end of the jaw slider block 54 can include an opening (not visible) for engagement with a distal end of a jaw power screw 70 that extends from a distal end of the flexible shaft 22. Thus, the opening in the jaw slider block 54 can include internal threads for engagement with the external threads of the distal end of the jaw power screw 70. Power screw 70 can be attached to the flexible shaft 22 via a coupler 72, which is visible in FIGS. 6 and 10, for example. The coupler 72 can include one of a number of different configurations that will allow shaft 22 and power screw 70 to be secured relative to each other to allow for a desired transfer of forces to the jaws 20 from the power screw 70.

Figure 9:
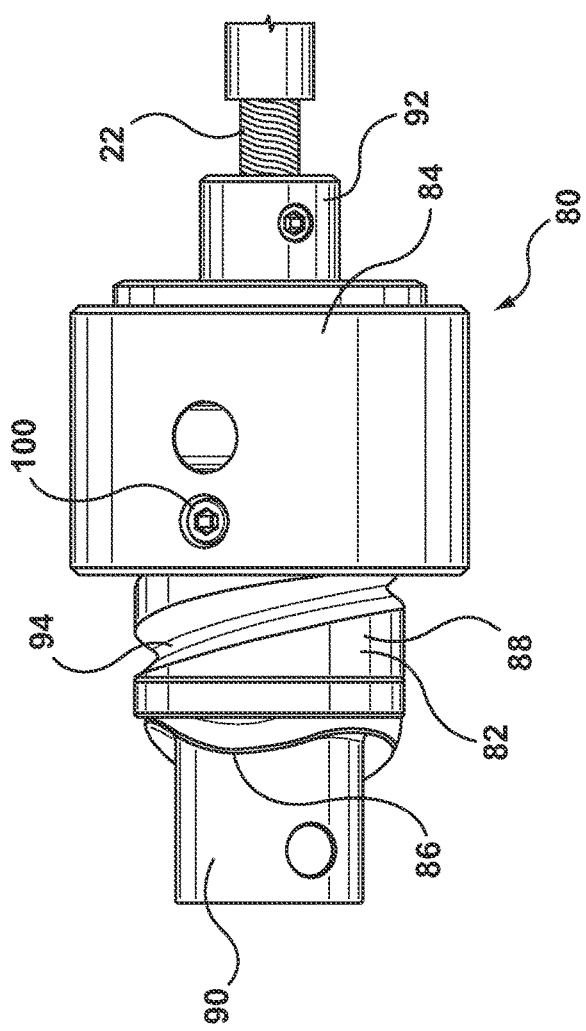
FIG. 9 is a perspective view of a screw mechanism of the handle portion of the ablation device illustrated in FIG. 8.

The proximal end of the flexible shaft 22 extends from a distal end of a handle power screw assembly 80, an enlarged view of which is illustrated in FIG. 9. The assembly 80 generally includes a handle power screw 82, a slider 84, and one or more return springs 86 positioned on a proximal end of the power screw 82. Handle power screw 82 includes a main body 88, a proximal flange 90, and a distal flange 92, wherein both of these flanges 90, 92 have a smaller diameter than that of the main body 88. The main body 88 of power screw 82 can be positioned relative to an interior opening of the slider 84 so that linear motion of the slider 84 will provide for rotation of the power screw 82 relative to the slider 84. The distal flange 92 is attachable to the proximal end of the flexible shaft 22 in a number of different ways, such as by providing the distal flange 92 with an internal opening that can accept and engage with the flexible shaft 22. In one embodiment, the flange 92 includes at least one setscrew that can extend into its inner area to engage with the flexible shaft and provide a secure connection between the shaft 22 and the flange 92.

Main body 88 includes at least one spiral channel 94 extending along at least a portion of its length. In one exemplary embodiment, the main body 88 includes three of such spiral channels 94 that are spaced evenly from each other around its surface, although more or less than three spiral channels can be provided. The channels 94 can be chamfered or angled, and can be sized (e.g., width and depth) to provide for secure engagement with protrusions that extend inwardly from an inner surface of the slider 84 (not visible). Such protrusions, which can include ball bearings, for example, can be adjustable from the outer surface of the slider 84, if desired, such as via a hole 100 in the slider 84 that can be manipulated to change the distance that such protrusions extend relative to the inner surface of the slider 84.

Figure 8:
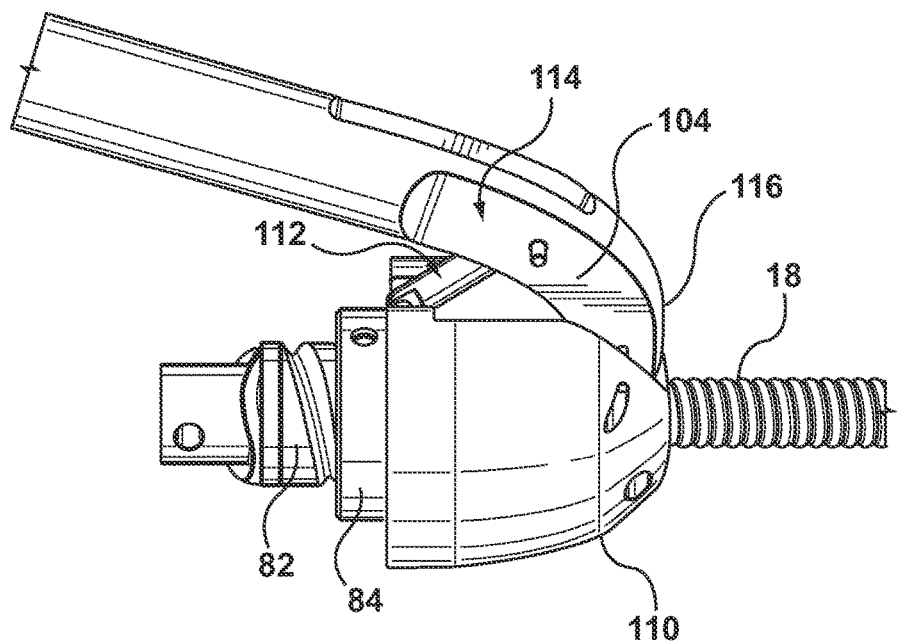
FIG. 8 is a front perspective view of a portion of the handle illustrated in FIG. 7, with a proximal portion of the handle cover removed.

Referring now to FIG. 8, the handle power screw assembly 80 is illustrated with a portion of a handle cover 110 surrounding a portion of its distal end, along with the neck 18 extending from the distal end of the handle cover 110. Handle cover 110 can include two or more body portions that are attached to each other to at least partially surround the handle power screw assembly 80. Handle cover 110 includes a slot on one side within which a lever 114 is attached at a pivot point 116. Movement of the lever 114 is further controlled by the use of a rod 112 that is attached at its first end to the lever 114 and at its second end to the slider 84. More particularly, the first end of rod 112 is attached to the lever 114 via a pivotal connection (e.g., the end of rod 112 is attached within a slot in the lever 114 through which a pin extends), while the second end of rod 112 is attached to the slider 84 via a flange member that extends from an outer surface of the slider 84. The connection between the second end of rod 112 is again provided as a pivotal connection. In this way, a 4-bar linkage configuration is provided within the handle, such that movement of any one of the components will cause a predefined corresponding movement in the other components that are included within the 4-bar linkage.

FIG. 7 includes the same components described relative to FIG. 8; however, FIG. 7 further illustrates the handle cover 110 as extending further in a proximal direction to completely cover the distal end of power screw assembly 80, along with providing a handle member that is sized and shaped to be easily be grasped by the user (e.g., a surgeon) to manipulate the ablation device 10. The handle cover 110 may be made of any of a wide variety of materials or combination of materials, such as metals, plastics, and the like, which materials are preferably non-conductive. The handle cover 110 may further include one or more internal passageways for lines or wires that extend from a power source for electrical connection to the jaws.

The jaws 20 can be assembled relative to the casing 30 so that when the jaws 20 are in a closed position, only an area adjacent to their distal tips 42 will contact each other and so that the inner surfaces 50 will be spaced from each other along the length of their respective elongated portions 40. With such a configuration, the inner surfaces 50 can either be parallel to each other or angled relative to each other when the jaws 20 are in their furthest open configuration, wherein the angle between the inner surfaces 50 will generally change when moving between the open and closed positions of the jaws 20.

As discussed above, the ablation device of the invention is not limited in its use to ablation procedures, but can also be used for cauterization procedures or other tissue treatment procedures. One use for ablation devices of the invention is to treat atrial fibrillation via ablation of atrial tissue. In particular, a lesion pattern can be created along certain areas of the atria by application of radiofrequency energy through specialized electrodes placed over the jaws that contact the desired treatment areas. In order to reach all of the desired areas within the patient, the surgeon can reconfigure the neck (e.g., before beginning any procedures) until a desired configuration is achieved. This neck generally will have enough rigidity to allow it to maintain this desired configuration until it is desired to reconfigure it.

Referring again to the exemplary device 10 illustrated in the Figures, after the neck 18 is in its desired shape, the distal tips of the jaws 20 can be moved toward the target tissue site. If the surgeon requires that the jaws 20 are in a closed position during the treatment procedure and/or when traveling along a path to a treatment site, the lever 114 of the handle 16 can be squeezed toward the handle body. This will cause the slider 84 of the power screw assembly 80 to linearly translate in a proximal direction. This movement, in turn, will pull the flexible shaft and its extending jaw power screw 70 in a proximal direction, thereby pulling the jaw slider block 54 and the attached jaws 20 in a proximal direction. This movement will cause the jaws 20 to also move closer to each other. When it is desired to then open the jaws, such as prior to clamping on to a target tissue, the lever 114 of the handle 16 can be released. This will cause the components to reverse their previous motions, thereby causing the jaw slider block 54 and the slider 84 to move in a distal direction. Any return spring(s) provided in the handle portion of the device 10 can assist in returning the various components of the device to a previous configuration without requiring the application of a force that is opposite from the force that was applied to displace the components.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of performing a surgical procedure using an instrument, comprising the steps of:
   receiving an instrument comprising:
   a proximal end;
   a distal end;
   a handle adjacent to the proximal end of the instrument;
   a flexible elongated neck extending distally from a distal end of the handle;
   a jaw power screw extending from a distal end of the neck to a slider block;
   a pair of moveable jaws including a first jaw and a second jaw; the pair of moveable jaws operatively connected to the jaw power screw with the slider block; wherein a first pin extends into both of the jaws to pivotally connect the jaws to the slider block;
   a casing; wherein the slider block and at least a portion of each of the pair of jaws are positioned within the casing; further wherein a second pin slidably connects the first jaw to the casing and a third pin slidably connects the second jaw to the casing; wherein the first pin is proximally positioned with respect to the second and third pins; and
   a handle power screw assembly operatively connected to a proximal end of the flexible neck within the handle;
   configuring the neck for access to a surgical site;
   maneuvering the distal end of the instrument to the surgical site with the jaws in a first position;
   manipulating the handle to move the jaws from the first position to a second position; and
   performing a desired therapy with the jaws at the surgical site.

2. The method of claim 1, wherein the step of manipulating the handle further comprises moving the jaws toward and away from each other while simultaneously translating the jaws in an axial direction relative to the distal end of the instrument.

3. The method of claim 1, wherein the therapy being performed comprises one of tissue ablation and tissue cauterization.

4. The method of claim 1, wherein the handle power screw assembly comprises:
   a handle power screw that comprises a main body having at least one spiral channel extending along its length; and
   a slider positioned to circumferentially surround at least a portion of the main body; and
   further comprising the step of initiating linear motion of the slider to rotate the handle power screw.

5. The method of claim 4, wherein the slider includes an inner tubular surface from which at least one protrusion extends that is engaged with at least one of the at least one spiral channel of the main body of the handle power screw.

6. The method of claim 1, wherein each of the first and second jaws includes a slot and the second and third pins respectively extend into the slots of the first and second jaws respectively.

7. The method of claim 1, wherein the second and third pins extending through the casing.

8. A method of performing a surgical procedure using an instrument, comprising the steps of:
   receiving an instrument comprising:
   a proximal end;
   a distal end;
   a handle adjacent to the proximal end of the instrument;
   a flexible elongated neck extending distally from a distal end of the handle;
   a jaw power screw extending from a distal end of the neck;
   a pair of moveable jaws including a first jaw and a second jaw; wherein the pair of moveable jaws are pivotally connected with a first pin; wherein each jaw includes a slot and the pair of jaws are operatively connected to the jaw power screw utilizing a casing, wherein the casing comprises second and third pins extending therefrom, wherein the second pin slidably connects the first jaw to the casing and the third pin slidably connects the second jaw to the casing; further wherein the first pin is proximally positioned with respect to the second and third pins; and
   a handle power screw assembly operatively connected to a proximal end of the flexible neck within the handle;
   configuring the neck for access to a surgical site;
   maneuvering the distal end of the instrument to the surgical site with the jaws in a first position;
   manipulating the handle to move the jaws relative to each other from the first position to a second position such that the pins slide in the slots; and
   performing a desired therapy with the jaws at the surgical site.

9. The method of claim 8, wherein the step of manipulating the handle further comprises moving the jaws toward and away from each other while simultaneously translating the jaws in an axial direction relative to the distal end of the instrument.

10. The method of claim 8, wherein the therapy being performed comprises one of tissue ablation and tissue cauterization.

11. The method of claim 8, wherein the handle power screw assembly comprises:
    a handle power screw that comprises a main body having at least one spiral channel extending along its length; and
    a slider positioned to circumferentially surround at least a portion of the main body; and
    further comprising the step of initiating linear motion of the slider to rotate the handle power screw.

12. The method of claim 11, wherein the slider includes an inner tubular surface from which at least one protrusion extends that is engaged with at least one of the spiral channels of the main body of the handle power screw.

* * * * *